United States Patent
Kaltenbach et al.

[11] Patent Number: 5,641,400
[45] Date of Patent: *Jun. 24, 1997

[54] USE OF TEMPERATURE CONTROL DEVICES IN MINIATURIZED PLANAR COLUMN DEVICES AND MINIATURIZED TOTAL ANALYSIS SYSTEMS

[75] Inventors: Patrick Kaltenbach, Bischweier, Germany; Sally A. Swedberg, Los Altos, Calif.; Klaus E. Witt, Keltern; Fritz Bek, Waldbronn, both of Germany; Laurie S. Mittelstadt, Belmont, Calif.

[73] Assignee: Hewlett-Packard Company, Palo Alto, Calif.

[*] Notice: The term of this patent shall not extend beyond the expiration date of Pat. No. 5,571,410.

[21] Appl. No.: 546,629

[22] Filed: Oct. 23, 1995

Related U.S. Application Data

[63] Continuation-in-part of Ser. No. 326,111, Oct. 19, 1994, Pat. No. 5,500,071.
[51] Int. Cl.[6] .................................................. B01D 15/08
[52] U.S. Cl. .................. 210/198.2; 210/656; 204/451; 204/601; 422/69; 422/70
[58] Field of Search .......................... 204/601, 602, 204/603, 604, 605, 451, 452, 453, 454, 455, 456; 210/635, 656, 659, 198.2; 422/68.1, 69, 70

[56] References Cited

U.S. PATENT DOCUMENTS

| | | | |
|---|---|---|---|
| 4,891,128 | 1/1990 | Sethi et al. | 204/299 |
| 4,908,112 | 3/1990 | Pace | 204/299 |
| 4,931,328 | 6/1990 | Swedberg | 204/601 |
| 5,006,313 | 4/1991 | Swedberg | 204/601 |
| 5,132,012 | 7/1992 | Miura et al. | 55/386 |
| 5,180,480 | 1/1993 | Manz | 204/644 |
| 5,194,133 | 3/1993 | Clark et al. | 204/299 |
| 5,198,091 | 3/1993 | Burolla | 204/601 |
| 5,291,226 | 3/1994 | Schantz et al. | 346/140 |
| 5,305,015 | 4/1994 | Schantz et al. | 346/140 |
| 5,376,252 | 12/1994 | Ekstrom | 210/198.2 |
| 5,500,071 | 3/1996 | Kaltenbach | 210/198.2 |

FOREIGN PATENT DOCUMENTS

| | | | |
|---|---|---|---|
| WO93/22058 | 11/1993 | WIPO | 210/198.2 |
| WO94/05414 | 3/1994 | WIPO | 210/198.2 |

OTHER PUBLICATIONS

Becker, E.W., et al., "Fabrication of Microstructures with High Aspect Ratios and Great Structural Heights by Synchrotron Radiation Lithography, Galvanoforming, and Plastic Moulding (LIGA Process)" *Microelectric Engineering* (1986) 4:35–56.
Beckers et al. (1988) *J. Chromatogr.* 452:591–600.
Burggraf et al. (1994) "A Novel Approach to Ion Separations in Solution: Synchronized Cyclic Capillary Electrophoresis (SCCE)" *Sensors and Actuators* B20:103–110.
Edmonds (1985) *Trends Anal. Chem.* 4:220.
Effenhauser et al. (1993) "Glass Chips for High-Speed Capillary Electophoresis Separations with Submicrometer Plate Heights" *Anal. Chem.* 65:2637–2642.
Fan et al., "Micromachining of Capillary Electrophoresis Injectors and Separators on Glass Chips and Evaluation of Flow at Capillary Intersections" *Anal Chem.* 66:(1):177–184 (1994).
Fillipini et al (1991) *J. Biotechnol.* 18:153.
Garn et al (1989) *Biotechnol. Bioeng.* 34:423.
Guibault (1983) *Anal. Chem Symp. Ser.* 17:637.
Ghowsi et al. (1990) *Anal. Chem.* 62:2714.

(List continued on next page.)

*Primary Examiner*—Ernest G. Therkorn

[57] ABSTRACT

Miniaturized planar column devices and miniaturized total analysis systems for liquid phase analysis are disclosed. The systems include a temperature control device for regulating temperature, preferably a thermoelectric device comprising Peltier elements.

24 Claims, 8 Drawing Sheets

OTHER PUBLICATIONS

Harrison et al. (1993) "Micromachining a Miniaturized Capillary Electrophoresis–Based Chemical Analysis System on a Chip" *Science* 261:895–897.

Harrison et al., "Towards Miniaturized Electrophoresis and Chemical Analysis Systems on Silicon: an Alternative to Chemical Sensors" *Sens. Actuators*, B10(2):107–116 (1993).

Jorgenson et al. (1983) *J. Chromatogr.* 255:335.

Knox et al. (1979) *J. Chromatogr.* 186:405.

Manz et al., "Planar Chips Technology for Miniaturization of Separation Systems: A Developing Perspective in Chemical Monitoring" *Adv. Chrom.* 33:1–66 (1993).

Manz et al., "Micromachining of Monocrystalline Silicon and Glass for Chemical Analysis Systems—A Look into Next Century's Technology or Just a Fashionable Craze?" *Trends Anal. Chem.* 10(5):144–149 (1991).

Manz et al., "Design of an Open–tubular Column Liquid Chromatograph using Silicon Chip Technology" *Sensors and Actuators B (Chemical)* B1(1–6):249–255 (1990).

Manz et al. (1992) *J. Chromatogr.* 593:253.

Müller et al. (1991) *J. High Resolut. Chromatogr.* 14:174.

Nelson et al. (1989) "Use of Peltier Thermoelectric Devices to Control Column Temperature in High–Performance Capillary Electrophoresis," *J. Chromatogr.* 480:111–127.

Olefirowicz et al. (1990) *Anal. Chem.* 62:1872.

Second Int'l Symp. High–Perf. Capillary Electrophoresis (1990) *J. Chromatogr.* 516.

Stinshoff et al. (1985) *Anal. Chem.* 57:114R.

Tshulena (1988) *Phys. Scr.* T23:293.

Tsuda et al. (1978) *Anal. Chem.* 50:632.

Widmer (1983) *Trends Anal. Chem.* 2:8.

Widmer et al. (1984) *Int. J. Environ. Anal. Chem.* 18:1.

Wilding et al. (1994), "PCR in a Silicon Microstructure," *Clin. Chem.* 40:1815–1818.

Znotins et al., *Laser Focus Electro Optics*, (1987) pp. 54–70.

USE OF TEMPERATURE CONTROL DEVICES IN MINIATURIZED PLANAR COLUMN DEVICES AND MINIATURIZED TOTAL ANALYSIS SYSTEMS

CROSS-REFERENCE TO RELATED APPLICATIONS

This application is a continuation-in-part of U.S. patent application Ser. No. 08/326,111, filed Oct. 19, 1994 now U.S. Pat. No. 5,500,071, from which priority is claimed pursuant to 35 U.S.C. §120, and which disclosure is hereby incorporated by reference in its entirety.

TECHNICAL FIELD

The present invention relates generally to miniaturized planar column technology and miniaturized total analysis systems for liquid phase analysis. More particularly, the invention relates to a liquid phase sample separation apparatus that includes a miniaturized planar column or a miniaturized total analysis system and a temperature control device for regulating the temperature in the separation apparatus.

BACKGROUND

In sample analysis instrumentation, and especially in separation systems such as liquid chromatography and capillary electrophoresis systems, smaller dimensions will generally result in improved performance characteristics and at the same time result in reduced production and analysis costs. In this regard, miniaturized separation systems provide more effective system design, result in lower overhead due to decreased instrumentation sizing and additionally enable increased speed of analysis, decreased sample and solvent consumption and the possibility of increased detection efficiency.

Accordingly, several approaches towards miniaturization for liquid phase analysis have developed in the art; the conventional approach using drawn fused-silica capillary, and an evolving approach using silicon micromachining. What is currently thought of as conventional in miniaturization technology is generally any step toward reduction in size of the analysis system.

In conventional miniaturized technology the instrumentation has not been reduced in size; rather, it is the separation compartment size which has been significantly reduced. As an example, micro-column liquid chromatography (µLC) has been described wherein columns with diameters of 100–200 µm are employed as compared to prior column diameters of around 4.6 mm.

Another approach towards miniaturization has been the use of capillary electrophoresis (CE) which entails a separation technique carried out in capillaries 25–100 µm in diameter. CE has been demonstrated to be useful as a method for the separation of small solutes. *J. Chromatogr.* 218:209 (1981); *Analytical Chemistry* 53:1298 (1981). In contrast, polyacrylamide gel electrophoresis was originally carried out in tubes 1 mm in diameter. Both of the above described "conventional" miniaturization technologies (µLC and CE) represent a first significant step toward reducing the size of the chemical portion of a liquid phase analytical system. A major drawback in the available approaches to miniaturization involves the chemical activity and chemical instability of silicon dioxide ($SiO_2$) substrates, such as silica, quartz or glass, which are commonly used in both CE and µLC systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pHs greater than 7.0).

However, despite the recognized shortcomings with the chemistry of $SiO_2$ substrates, those materials are still used in separation systems due to their desirable optical properties. In this regard, potential substitute materials which exhibit superior chemical properties compared to silicon dioxide materials are generally limited in that they are also highly adsorbing in the UV region, where detection is important.

In order to avoid some of the substantial limitations present in conventional µLC and CE techniques, and in order to enable even greater reduction in separation system sizes, there has been a trend towards providing planarized systems having capillary separation microstructures. In this regard, production of miniaturized separation systems involving fabrication of microstructures in silicon by micromachining or microlithographic techniques has been described. See, e.g. Fan et al., *Anal. Chem.* 66(1):177–184 (1994); Manz et al., *Adv. Chrom.* 33:1–66 (1993); Harrison et al., *Sens. Actuators*, B10(2):107–116 (1993); Manz et al., *Trends Anal. Chem.* 10(5):144–149 (1991); and Manz et al., *Sensors and Actuators B (Chemical)* B1(1–6):249–255 (1990).

Recently, sample preparation technologies have been successfully reduced to miniaturized formats. Gas chromatography (Widmer et al. (1984) *Int. J. Environ. Anal. Chem.* 18:1), high pressure liquid chromatography (Müller et al. (1991) *J. High Resolut. Chromatogr.* 14: 174; Manz et al. . (1990) *Sensors & Actuators* B1:249; Novotny et al., eds. (1985) *Microcolumn Separations: Columns, Instrumentation and Ancillary Techniques* (*J. Chromatogr. Library*, Vol. 30); Kucera, ed. (1984) *Micro-Column High Performance Liquid Chromatography*, Elsevier, Amsterdam; Scott, ed. (1984) *Small Bore Liquid Chromatography Columns: Their Properties and Uses*, Wiley, NY; Jorgenson et al. (1983) *J. Chromatogr.* 255:335; Knox et al. (1979) *J. Chromatogr.* 186:405; Tsuda et al. (1978) *Anal. Chem.* 50:632) and capillary electrophoresis (Manz et al. (1992) *J. Chromatogr.* 593:253; Manz et al. *Trends Anal. Chem.* 10:144; Olefirowicz et al. (1990) *Anal. Chem.* 62:1872; Second Int'l Symp. High-Perf. Capillary Electrophoresis (1990) *J. Chromatogr.* 516; Ghowsi et al. (1990) *Anal. Chem.* 62:2714) have been reduced to miniaturized formats.

Capillary electrophoresis has been particularly amenable to miniaturization because the separation efficiency is proportional to the applied voltage regardless of the length of the capillary. Harrison et al. (1993) Science 261:895–897. A capillary electrophoresis device using electroosmotic fluid pumping and laser fluorescence detection has been prepared on a planar glass microstructure. Effenhauser et al. (1993) *Anal. Chem.* 65:2637–2642; Burggraf et al. (1994) *Sensors and Actuators* B20:103–110. In contrast to silicon materials (see, Harrison et al. (1993) *Sensors and Actuators* B10:107–116), polyimide has a very high breakdown voltage, thereby allowing the use of significantly higher voltages.

State-of-the-art chemical analysis systems for use in chemical production, environmental analysis, medical diagnostics and basic laboratory analysis must be capable of complete automation. Such a total analysis system (TAS) (Fillipini et al (1991) *J. Biotechnol.* 18:153; Garnet al (1989) *Biotechnol. Bioeng.* 34:423; Tshulena (1988) *Phys. Scr.* T23:293; Edmonds (1985) *Trends Anal. Chem.* 4:220; Stinshoff et al. (1985) *Anal. Chem.* 57:114R; Guibault (1983) *Anal. Chem Symp.* Ser. 17:637; Widmer (1983) *Trends Anal. Chem.* 2:8) automatically performs functions ranging from introduction of sample into the system, transport of the sample through the system, sample preparation, separation, purification and detection, including data acquisition and evaluation. Miniaturized total analysis systems have been referred to as "µ-TAS."

Thermal effects have been recognized to influence many of the physical and chemical parameters involved in column separation techniques. The temperature of a column device can affect, among other things, sample stability, buffer viscosity, chemical equilibria, pH and the resulting migration time for a given chemical species.

Because of the small size of the miniaturized devices incorporated in the liquid sample apparatus disclosed herein, heating and/or cooling thereof can be extremely rapid and efficient. Temperature controlling devices can be used to provide overall heating or cooling of the apparatus, localized or regional heating or cooling and temperature gradients along the length of the separation chamber.

SUMMARY OF THE INVENTION

The present invention relates to a liquid phase sample separation apparatus. It is a primary object of the present invention to provide such an apparatus that includes a miniaturized column device laser-ablated in a substantially planar substrate, wherein said substrate is comprised of a material selected to avoid the inherent chemical activity and pH instability encountered with silicon and prior silicon dioxide-based device substrates, and a temperature control device capable of heating or cooling the miniaturized column device so as to provide temperature regulation over the entire surface of the column device, to provide regional temperature regulation, or to provide temperature regulation in such a manner as to generate a temperature gradient along the length of the miniaturized column device.

It is yet a further related object of the present invention to provide a liquid phase sample separation apparatus including a miniaturized total chemical analysis system (µ-TAS) fully contained on a single, planar surface and a temperature control device as described above. The µ-TAS is capable of performing complex sample handling, separation, and detection methods with reduced technician manipulation or interaction.

A particular advantage of the present invention is the use of processes other than silicon micromachining techniques or etching techniques to create miniaturized columns in a wide variety of polymeric and ceramic substrates having desirable attributes for an analysis portion of a separation system. More specifically, it is contemplated herein to provide a miniaturized planar column device or a µ-TAS by ablating component microstructures in a substrate using laser radiation. The device is in thermal communication with a temperature control device capable of heating or cooling the device so as to provide temperature regulation either over the entire surface of the device, to provide regional temperature regulation or to provide temperature regulation in such a manner as to generate a temperature gradient along the length of the miniaturized column device.

In one embodiment of the invention, a liquid phase sample separation apparatus is provided which incorporates (a) a miniaturized column device including a substrate having first and second substantially planar opposing surfaces wherein said substrate is a material other than silicon or silicon dioxide, said substrate having a microchannel laser-ablated in the first planar surface, a cover plate arranged over the first planar surface, said cover plate in combination with the microchannel defining an elongate separation compartment, and at least one inlet port and at least one outlet port communicating with the separation compartment, said ports enabling the passage of fluid from an external source through the separation compartment and (b) a temperature control device in thermal communication with the miniaturized column device.

In another embodiment of the invention, a liquid phase sample separation apparatus is provided which incorporates (a) a miniaturized column device including a substrate having first and second substantially planar and parallel opposing surfaces, wherein said substrate is a material other than silicon or silicon dioxide, said substrate having first and second microchannels respectively laser ablated in the first and second planar surfaces, a conduit means for communicating the first and second separation compartments with each other, thereby forming a single continuous separation compartment, said conduit means containing an aperture in the substrate having an axis which is orthogonal to the planar surfaces, and first and second cover plates disposed respectively over the first and second planar surfaces, said cover plates in combination with the first and second microchannels defining first and second elongate separation compartments and (b) a temperature control device in thermal communication with the column device.

In yet another embodiment of the invention, a liquid phase sample separation apparatus which incorporates (a) a miniaturized column device including a support body formed from a substrate of a material other than silicon or silicon dioxide, said support body having first and second component halves each having substantially planar interior surfaces, a first microchannel laser-ablated in the interior surface of the first support body half and a second microchannel laser-ablated in the interior surface of the second support body half, wherein each said microchannel is so arranged as to provide the mirror image of the other, a separation compartment containing an elongate bore formed by aligning the interior surfaces of the support body halves in facing abutment with each other whereby the microchannels define said elongate bore, and at least one inlet port and at least one outlet port communicating with the separation compartment, said ports enabling the passage of fluid from an external source through the separation compartment and (b) a temperature control device in thermal communication with the column device.

In a further embodiment of the invention, a liquid phase sample separation apparatus is provided incorporating (a) a miniaturized total analysis system (µ-TAS) integrating a miniaturized column device including a substrate having first and second substantially planar opposing surfaces wherein said substrate is a material other than silicon or silicon dioxide, said substrate having a first microchannel laser-ablated in the first planar surface, wherein said first microchannel comprises more than one sample handling region, a cover plate arranged over the first planar surface, said cover plate in combination with the first microchannel forming a first sample processing compartment, wherein the sample handling regions define a sample flow component in fluid communication with a sample treatment component and at least one inlet port and at least one outlet port communicating with the first sample processing compartment, said inlet and outlet ports enabling the passage of fluid from an external source through the sample processing compartment with (b) a temperature control device in thermal communication with the miniaturized column device.

DETAILED DESCRIPTION OF THE INVENTION

Figure 1:
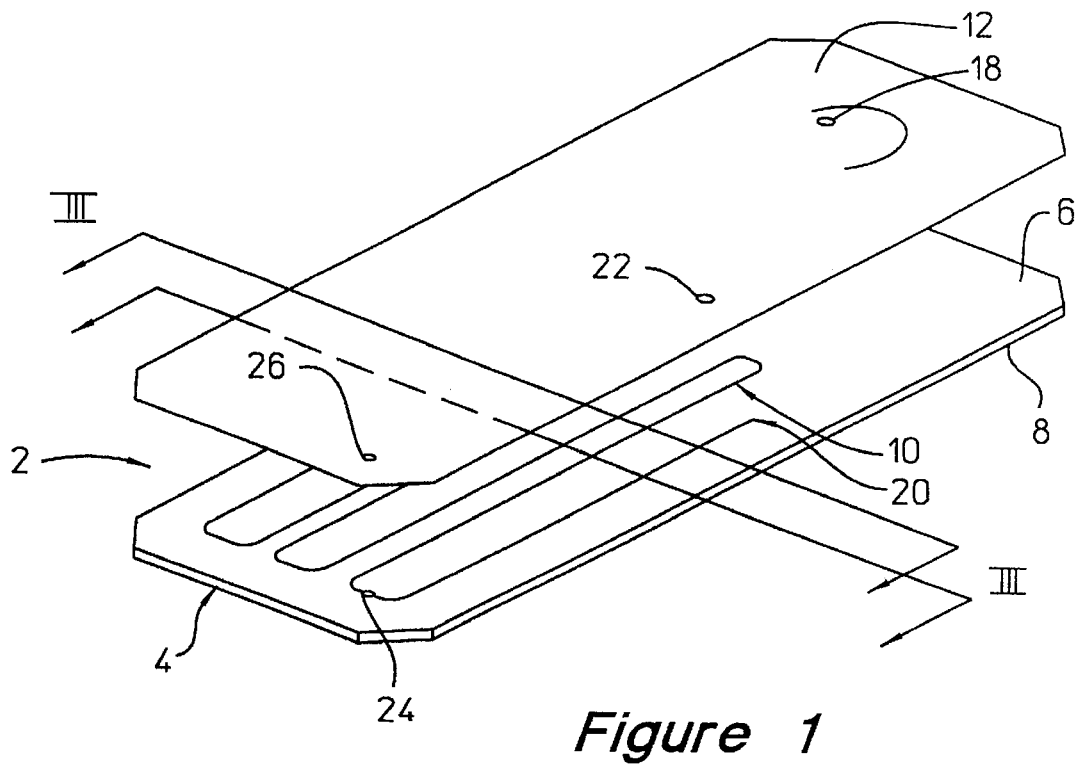
FIG. 1 is an exploded view of a miniaturized column device constructed in accordance with the present invention.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a thermoelectric heat exchange device" includes two or more such devices, reference to "a sample flow component" includes more than one such component, and the like.

In this specification and in the claims which follow, reference will be made to a number of terms which shall be defined to have the following meanings:

The term "substrate" is used herein to refer to any material which is UV-adsorbing, capable of being laser-ablated and which is not silicon or a silicon dioxide material such as quartz, fused silica or glass (borosilicates). Accordingly, miniaturized column devices are formed herein using suitable substrates, such as laser ablatable polymers (including polyimides and the like) and ceramics (including aluminum oxides and the like). Further, miniaturized column devices are formed herein using composite substrates such as laminates. A "laminate" refers to a composite material formed from several different bonded layers of same or different materials. One particularly preferred composite substrate comprises a polyimide laminate formed from a first layer of polyimide, such as Kapton® (DuPont; Wilmington, Del.), that has been co-extruded with a second, thin layer of a thermal adhesive form of polyimide known as KJ® (DuPont). This thermoplastic adhesive can be applied to one or both sides of the first polyimide layer, thereby providing a means for producing a laminate of desired thickness.

The term "sample handling region" refers to a portion of a microchannel, or to a portion of a "sample processing compartment" that is formed upon enclosure of the microchannel by a cover plate or substrate in which a mirror image of the microchannel has been laser ablated as described in detail below, that includes a "sample flow component" or a "sample treatment component." By the term "sample flow component" is intended a portion of the sample processing compartment that interconnects sample treatment components.

A "sample treatment component" is a portion of the sample processing compartment in which particular sample preparation chemistries are done. In particular, an analyte of interest is generally obtained in a matrix containing other species which may potentially interfere with the detection and analysis of the analyte. Accordingly, a sample treatment component is a portion of the sample processing compartment in which analyte separation from the matrix is effected. Examples of functions which may be served by the sample treatment component include chromatographic separations, electrophoretic separations, electrochromatographic separations, and the like.

As used herein, the term "detection means" refers to any means, structure or configuration which allows one to interrogate a sample within the sample processing compartment using analytical detection techniques well known in the art. Thus, a detection means includes one or more apertures, elongated apertures or grooves which communicate with the sample processing compartment and allow an external detection apparatus or device to be interfaced with the sample processing compartment to detect an analyte passing through the compartment.

An "optical detection path" refers to a configuration or arrangement of detection means to form a path whereby radiation, such as a ray of light, is able to travel from an external source to a means for receiving radiation-wherein the radiation traverses the sample processing compartment and can be influenced by the sample or separated analytes in the sample flowing through the sample processing compartment. An optical detection path is generally formed according to the invention by positioning a pair of detection means directly opposite each other relative to the sample processing compartment. In this configuration, analytes passing through the sample processing compartment can be detected via transmission of radiation orthogonal to the major axis of the sample processing compartment (and, accordingly, orthogonal to the direction of electro-osmotic flow in an electrophoretic separation). A variety of external optical detection techniques can be readily interfaced with the sample processing compartment using an optical detection path including, but not limited to, UV/Vis, Near IR, fluorescence, refractive index (RI) and Raman techniques.

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly electrophoretic separations contemplated for use in the invention include separations performed in columns packed with gels (such as polyacrylamide, agarose and combinations thereof) as well as separations performed in solution.

"Electrochromatographic" separation refers to combinations of electrophoretic and chromatographic techniques. Exemplary electrochromatographic separations include packed column separations using electromotive force (Knox et al. (1987) *Chromatographia* 24:135; Knox et al. (1989) *J. Liq. Chromatogr* 12:2435; Knox et al. (1991) *Chromatographia* 32:317), and micellar electrophoretic separations (Terabe et al. (1985) *Anal. Chem.* 57:834841).

The term "motive force" is used to refer to any means for inducing movement of a sample along a column in a liquid phase analysis, and includes application of an electric potential across any portion of the column, application of a pressure differential across any portion of the column or any combination thereof.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

In general, any substrate which is UV absorbing provides a suitable substrate in which one may laser ablate features. Accordingly, microstructures of selected configurations can be formed by imaging a lithographic mask onto a suitable substrate, such as a polymer or ceramic material, and then laser ablating the substrate with laser light in areas that are unprotected by the lithographic mask.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques have been described in the art. Znotins, T. A., et al., *Laser Focus Electro Optics*, (1987) pp. 54–70; U.S. Pat. Nos. 5,291,226 and 5,305,015 to Schantz et al. "Optional" or "optionally" means that the subsequently described feature or structure may or may not be present in the μ-TAS or that the subsequently described event or circumstance may or may not occur, and that the description includes instances where said feature or structure is present and instances where the feature or structure is absent, or instances where the event or circumstance occurs and instances where it does not. For example, the phrase "a μ-TAS optionally having detection means" intends that access ports may or may not be present on the device and that the description includes both circumstances where access ports are present and absent.

Accordingly, the invention concerns formation of miniaturized column devices including μ-TASs using laser ablation in a suitable substrate and providing a temperature control device in thermal contact therewith. It is also contemplated to form column devices and μ-TASs according to the invention using injection molding techniques wherein the original microstructure has been formed by an excimer laser ablation process, or where the original microstructure has been formed using a LIGA process.

More particularly, microstructures such as sample processing compartments, injection means, detection means and micro-alignment means may be formed in a planar substrate by excimer laser ablation. A frequency multiplied YAG laser may also be used in place of the excimer laser. In such a case, a complex microstructure pattern useful for practicing the invention may be formed on a suitable polymeric or ceramic substrate by combining a masking process with a laser ablation means, such as in a step-and-repeat process, where such processes would be readily understood by one of ordinary skill in the art.

In the practice of the invention, a preferred substrate comprises a polyimide material such as those available under the trademarks Kapton® or Upilex® from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof. Further, the polymer material selected may be produced in long strips on a reel, and, optional sprocket holes along the sides of the material may be provided to accurately and securely transport the substrate through a step-and-repeat process.

According to the invention, the selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and sample processing chambers.

Alternatively, patterns such as the aperture pattern, the sample processing channel pattern, etc., may be placed side by side on a common mask substrate which is substantially larger than the laser beam. Such patterns may then be moved sequentially into the beam. In other contemplated production methods, one or more masks may be used to form apertures through the substrates and another mask and laser energy level (and/or number of laser shots) may be used to define sample processing channels which are only formed through a portion of the thickness of the substrate. The masking material used in such masks will preferably be highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

It will be readily apparent to one of ordinary skill in the art that laser ablation may be used to form miniaturized sample processing channels and apertures in a wide variety of geometries. Any geometry which does not include undercutting may be provided using ablation techniques, such as modulation of laser light intensity across the substrate, stepping the beam across the surface or stepping the fluence and number of pulses applied to each location to control corresponding depth. Further, laser-ablated channels or chambers produced according to the invention are easily fabricated having ratios of channel depth to channel width which are much greater than previously possible using etching techniques such as silicon micromachining. Such aspect ratios can easily exceed unity, and may even reach to 10.

Furthermore, the aspect ratio of laser-ablated channels and chambers can be less than one, i.e., the width of the channel or chamber can be greater than the depth.

In a preferred embodiment of the invention, channels of a semi-circular cross section are laser ablated by controlling exposure intensity or by making multiple exposures with the beam being reoriented between each exposure. Accordingly, when a corresponding semicircular channel is aligned with a channel thus formed, a sample processing chamber of highly symmetrical circular cross-section is defined which may be desirable for enhanced fluid flow through the sample processing device.

As a final step in laser ablation processes contemplated by the invention, a cleaning step is performed wherein the laser-ablated portion of the substrate is positioned under a cleaning station. At the cleaning station, debris from the laser ablation are removed according to standard industry practice.

As will be appreciated by those working in the field of liquid phase analysis devices, the above-described method may be used to produce a wide variety of miniaturized devices. One such device is represented in FIG. 1 where a particular embodiment of a miniaturized column device is generally indicated at 2. Generally, miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

In a particular embodiment of the invention, the miniaturized column device 2 comprises a column structure ablated on a chip, which, in the practice of the invention may be a machinable form of the plastic polyimide such as Vespel®. It is particularly contemplated in the invention to use such a polyimide substrate as, based on considerable experience with the shortcomings of fused silica and research into alternatives thereof, polyimides have proved to be a highly desirable substrate material for the analysis portion of a liquid phase sample processing system.

In this regard, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which may provide a variety of desirable surface properties, depending on the target analysis. Unlike prior silicon dioxide based systems, these bonds to the polymeric substrate demonstrate pH stability in the basic region (pH 9–10).

Figure 2:
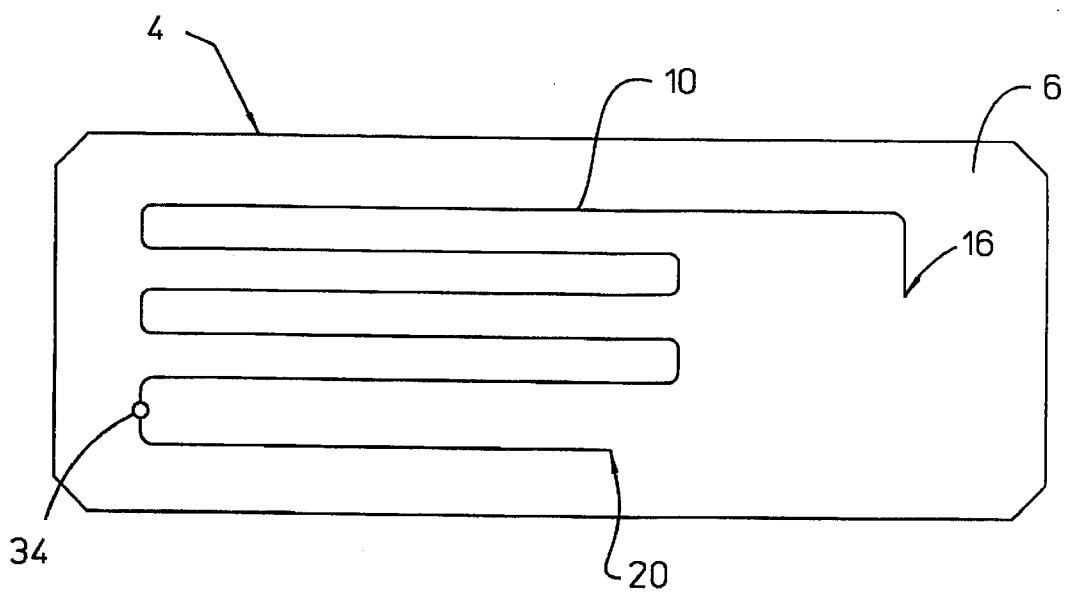
FIG. 2 is a plan view of the interior surface of the miniaturized column device of FIG. 1.
Figure 3:
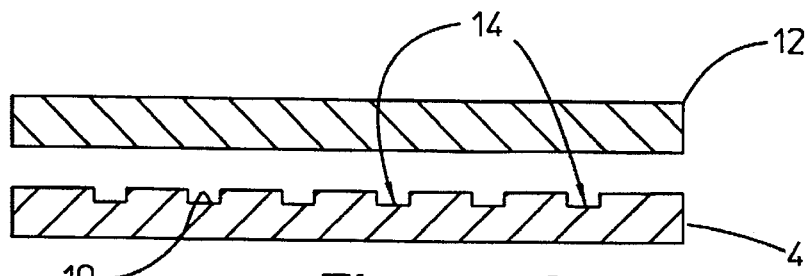
FIG. 3 is a cross-sectional side view of the miniaturized column device of FIG. 1, taken along lines III—III and showing formation of a sample processing compartment according to the invention.

Referring now to FIG. 1, FIG. 2 and FIG. 3, the substrate 4 has a microchannel 10 laser-ablated in a first planar surface 6. It will be readily appreciated that, although the microchannel 10 has been represented in a generally extended form, microchannels formed according to the invention may be ablated in a large variety of configurations, such as in a straight, serpentine, spiral, or any tortuous path desired. Further, as described in greater detail above, the microchannel 10 may be formed in a wide variety of channel geometries including semi-circular, rectangular, rhomboid, and the like, and the channels may be formed in a wide range of aspect ratios. It is also noted that a device having a plurality of microchannels laser-ablated thereon falls within the spirit of the present invention.

Referring particularly to FIG. 1, a cover plate 12 is arranged over said first planar surface 6 and, in combination with the laser-ablated microchannel 10, forms an elongate sample processing compartment 14. Cover plate 12 may be formed from any suitable substrate such as polyimide, the selection of the substrate only being limited by avoidance of undesirable separation surfaces such as silicon or silicon dioxide materials.

According to the invention, cover plate 12 may be fixably aligned over the first planar surface 6 to form a liquid-tight sample processing compartment by using pressure sealing techniques, by using external means to urge the pieces together (such as clips, tension springs or associated clamping apparatus) or by using adhesives well known in the art of bonding polymers, ceramics and the like.

Referring to FIG. 1, FIG. 2 and FIG. 3, a particular embodiment of the invention is shown wherein cover plate 12 further comprises apertures ablated therein. In this regard, a first aperture communicates with the sample processing compartment 14 at a first end 16 thereof to form an inlet port 18 enabling the passage of fluid from an external source into said sample processing compartment. A second aperture communicates with the sample processing compartment 14 at a second end 20 thereof to form an outlet port 22 enabling passage of fluid from the sample processing compartment to an external receptacle. Accordingly, a miniaturized column device is formed having a flow path extending from the first end 16 of the sample processing compartment and passing to the second end 20 thereof, whereby liquid phase analysis of samples may be carried out using techniques well known in the art.

Accordingly, in the practice of the invention, external hardware provides the mechanical valving necessary for communication of a miniaturized column device to different external liquid reservoirs, such as an electrolyte solution, flush solution or the sample via laser-ablated holes designed into the cover plate 12. This feature allows a variety of injection methods to be adapted to a miniaturized planar column device constructed according to the invention, including pressure injection, hydrodynamic injection or electrokinetic injection. In the particular embodiment of FIG. 1, FIG. 2 and FIG.3, it is contemplated that external valving and injection means communicate with the sample processing device by butt-coupling to the laser-ablated apertures, however, any other suitable methods of connection known in the art may easily be adapted to the invention. Further, it is noted that numerous other sample introduction and fluid interfacing designs may be practiced and still fall within the spirit of the subject invention.

Also according to the invention, a wide variety of means for applying a motive force along the length of the sample processing compartment 14 may be associated with the subject device. In this regard, a pressure differential or electric potential may be applied along the entire length of the sample processing compartment by interfacing motive means with inlet port 18 and outlet port 22.

The use of substrates such as polyimides in the construction of miniaturized columns according to the invention allows the possibility of using refractive-index (RI) detection to detect separated analytes of interest passing through the subject columns. In this regard, the provision of an associated laser diode which emits radiation at a wavelength where polyimide is "transparent" (such as at >500 nm) allows for a detection setup where no additional features need to be ablated in the column devices.

Referring now to FIG. 2 and FIG. 3, in a preferred embodiment of the invention, detection means may be ablated into the substrate 4 and cover plate 12, where said detection means is disposed substantially downstream of the first end 16 of the sample processing compartment 14. More particularly, an aperture 24 may be ablated through substrate 4 to communicate with the sample processing compartment 14. A corresponding aperture 26 may be likewise formed in cover plate 12, and arranged so that it will be in co-axial alignment with aperture 24 when the cover plate is affixed to the substrate to form the sample processing compartment 14. In this manner, electrodes (not shown) may be connected to the miniaturized column device via the apertures 24 and 26 to detect separated analytes of interest passing through the sample processing compartment by electrochemical detection techniques.

Figure 4A:
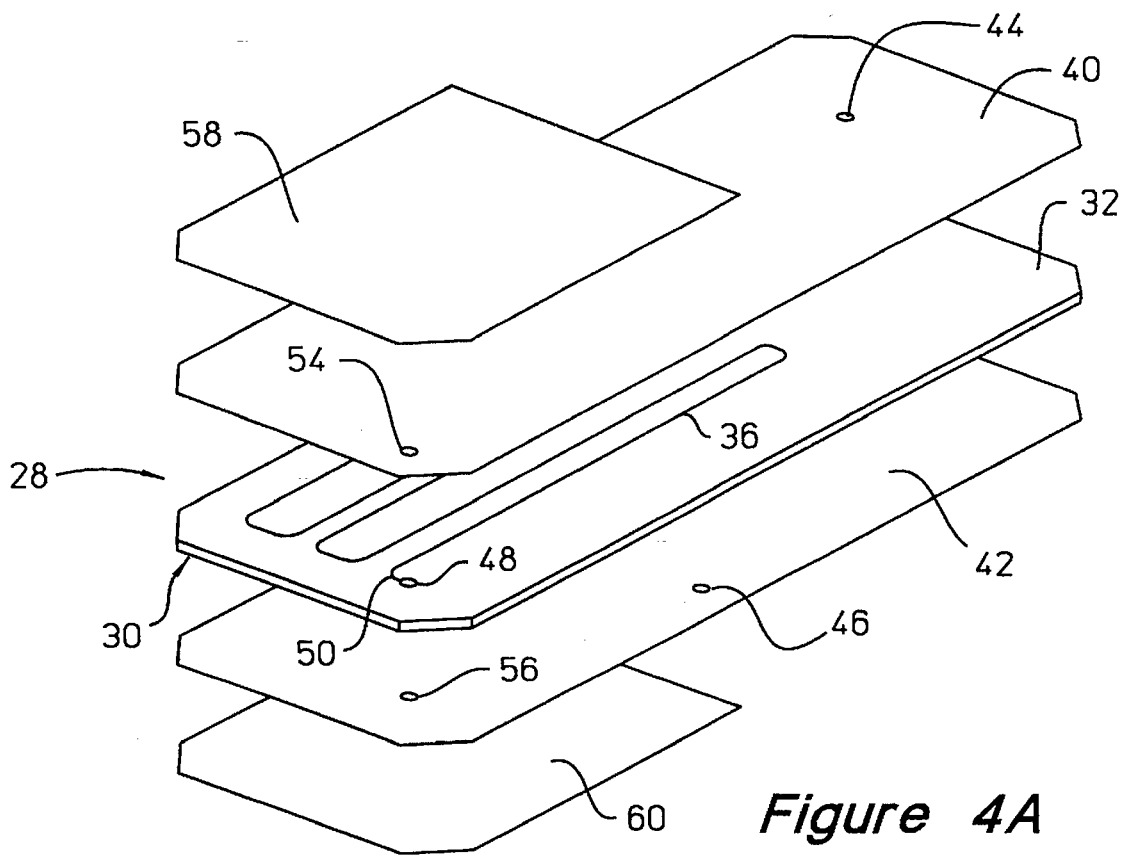
FIG. 4A is an exploded view of a first side of a miniaturized column device having microchannels formed on two opposing planar surfaces of a support substrate.
Figure 4B:
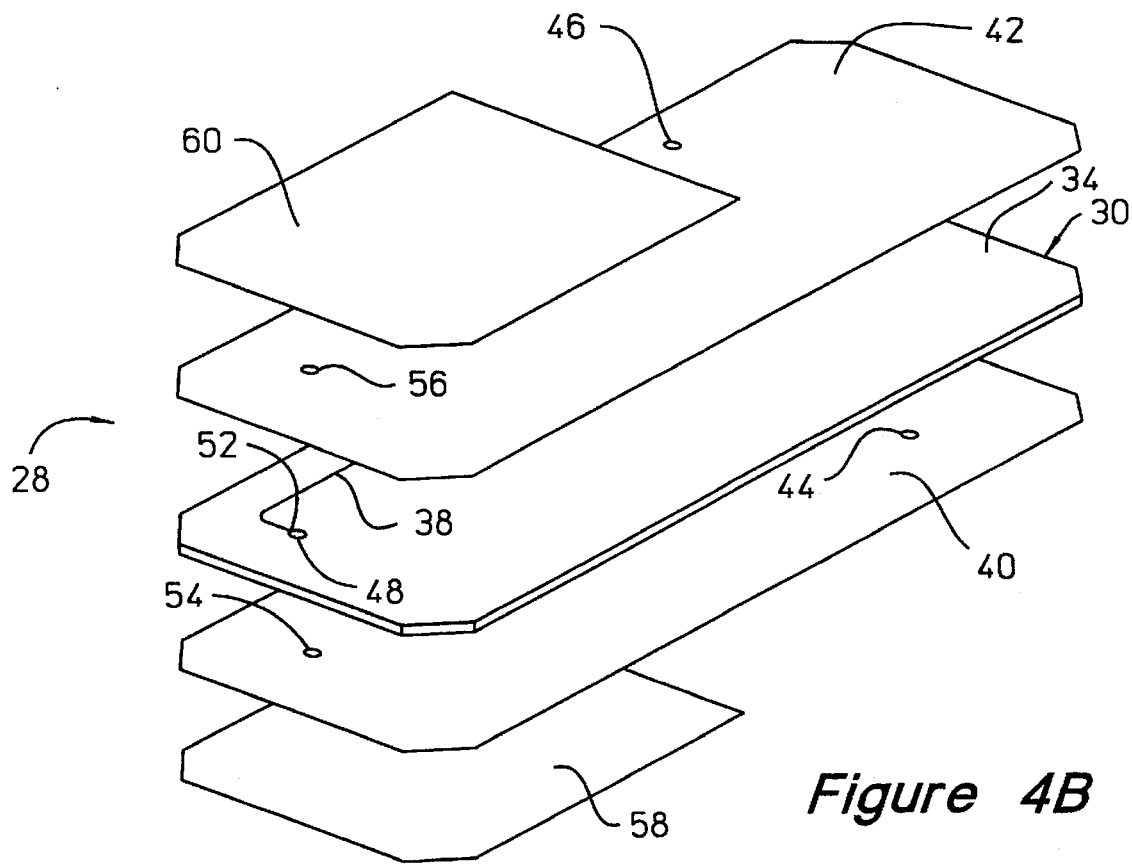
FIG. 4B is an exploded view of a second side of the column device of FIG. 4A.

FIG. 4A and FIG. 4B show a further embodiment of a miniaturized column device is generally indicated at 28. The miniaturized column comprises a substrate 30 having first and second substantially planar opposing surfaces respectively indicated at 32 and 34. The substrate 30 has a first microchannel 36 laser ablated in the first planar surface 32 and a second microchannel 38 laser ablated in the second planar surface 34, wherein the microchannels can be provided in a wide variety of geometries, configurations and aspect ratios as described above.

The miniaturized column device of FIG. 4A and FIG. 4B further includes first and second cover plates, indicated at 40 and 42 respectively, which, in combination with the first and second microchannels 36 and 38, define first and second elongate separation compartments when substrate 30 is sandwiched between the first and second cover plates.

Referring still to FIG. 4A and FIG. 4B, a plurality of apertures can be laser-ablated in the device to provide an extended separation compartment, and further to establish fluid communication means. More particularly, a conduit means 48, comprising a laser ablated aperture in substrate 30 having an axis which is orthogonal to the first and second planar surfaces 32 and 34, communicates a distal end 50 of the first microchannel 36 with a first end 52 of the second microchannel 38 to form an extended separation compartment.

Further, an aperture 44, laser ablated in the first cover plate 40, enables fluid communication with the first microchannel 36, and a second aperture 46, laser ablated in the second cover plate 42, enables fluid communication with the second microchannel 38. As will be readily appreciated, when the aperture 44 is used as an inlet port, and the second aperture 46 is used as an outlet port, a miniaturized column device is provided having a flow path extending along the combined length of the first and second microchannels 36 and 38.

In the embodiment of the invention as shown in FIG. 4A and FIG. 4B, a wide variety of sample introduction means can be employed, such as those described above. External hardware can also be interfaced to the subject device to provide liquid handling capabilities, and a variety of means for applying a motive force along the length of the separation compartment can be associated with the device, such as by interfacing motive means with the first and/or second apertures 44 and 46 as described above.

Additionally, a variety of detection means are easily included in the subject embodiment. In this regard, a first aperture 54 can be laser ablated in the first cover plate 40, and a second aperture 56 can likewise be formed in the second cover plate 42 such that the first and second apertures will be in co-axial alignment with conduit means 48 when the substrate 30 is sandwiched between the first and second cover plates. Detection of analytes in a separated sample passing through the conduit means is thereby easily enabled, such as by connecting electrodes to the miniaturized column via apertures 54 and 56 and detecting using electrochemical techniques.

However, a key feature of the laser-ablated conduit means 48 is the ability to provide an extended optical detection path length of up to 1 mm, or greater, without experiencing untoward sample plug distortion due to increased separation compartment volumes at the point of detection. Referring to FIG. 4A and FIG. 4B, first and second transparent sheets, indicated at 58 and 60 respectively, can be provided such that the first cover plate 40 is interposed between the first transparent sheet and the first planar surface 32, and the second cover plate 42 is interposed between the second transparent sheet and the second planar surface 34. The transparent sheets 58 and 60 can be selected from appropriate materials such as quartz crystal, fused silica, diamond, sapphire and the like. Further, the transparent sheets can be provided having just enough surface area to cover and seal the apertures 54 and 56, or those sheets can be sized to cover up to the entire surface area of the column device. As described above, this feature allows additional structural rigidity to be provided to a column device formed in a particularly thin substrate.

Figure 5A:
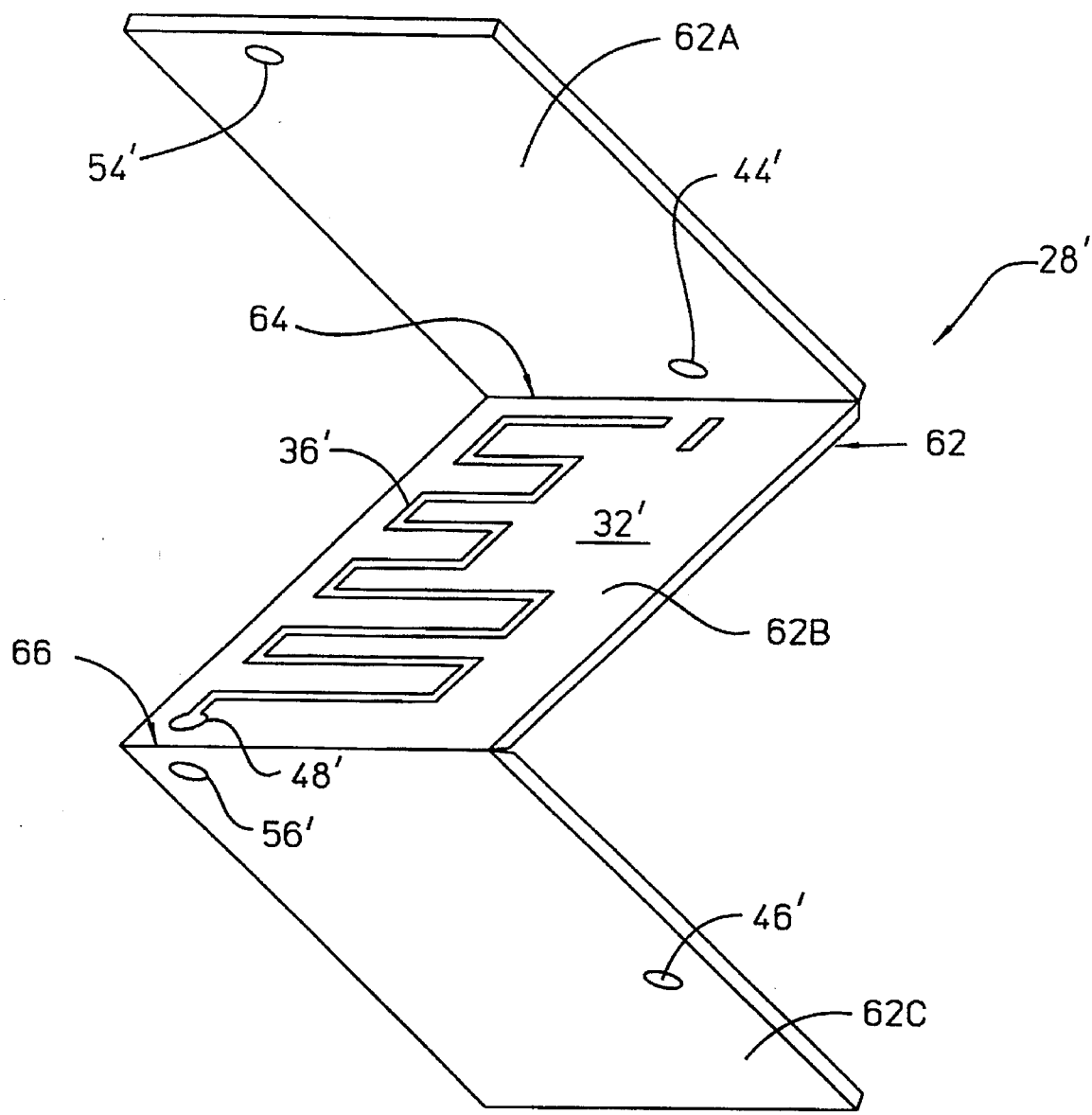
FIG. 5A is a pictorial representation of a first side of a preferred embodiment of the miniaturized column device of FIG. 4A which is constructed from a single flexible substrate.
Figure 5B:
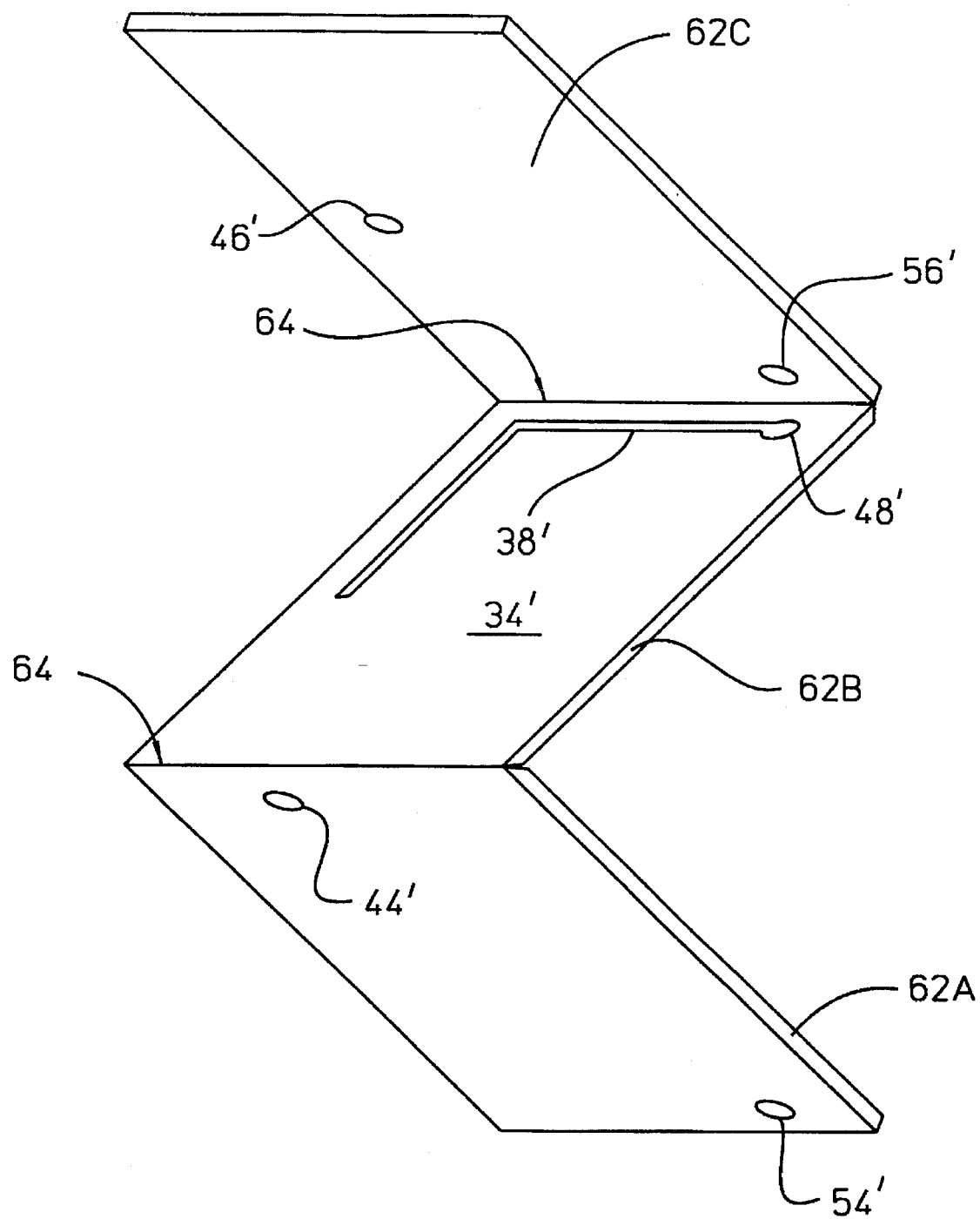
FIG. 5B is a pictorial representation of a second side of the column device of FIG. 5A.

Referring now to FIG. 5A and FIG. 5B, a related embodiment of the invention is shown, comprising a miniaturized column device 28', wherein the column portion and the first and second cover plates are formed in a single, flexible substrate generally indicated at 62. The flexible substrate 62 thus comprises three distinct regions, a column portion 62B, having first and second substantially planar opposing surfaces 32' and 34', respectively, where the column portion is interposed between a first cover plate portion 62A and a second cover plate portion 62C. The first and second cover plate portions have at least one substantially planar surface. The first cover plate portion 62A and the column portion 62B are separated by at least one fold means 64 such that the first cover plate portion can be readily folded to overlie the first substantially planar surface 32' of the column portion 62B. The second cover plate portion 62C and the column portion 62B are likewise separated by at least one fold means 66 such that the second cover plate can be readily folded to overlie the second substantially planar surface 34' of the column portion 62B. In particularly preferred embodiments, each fold means 64 and 66 can comprise a row of spaced-apart perforations ablated in the flexible substrate, spaced-apart slot-like depressions or apertures ablated so as to extend only part way through the substrate, or the like. The perforations or depressions can have circular, diamond, hexagonal or other shapes that promote hinge formation along a predetermined straight line.

Thus, the miniaturized column device 28' is formed by laser ablating a first microchannel 36' in the first planar surface 32' of the column portion 62B, and a second microchannel 38' in the second planar surface 34' of the column portion. Each microchannel can be provided in a wide variety of geometries, configurations and aspect ratios. A first separation compartment is then formed by folding the flexible substrate 62 at the first fold means 64 such that the first cover plate portion 62A covers the first microchannel 36' to form an elongate separation compartment. A second separation compartment is then provided by folding the flexible substrate 62 at the second fold means 66 such that the second cover plate portion 62C covers the second microchannel 38' to form a separation compartment as described above. A conduit means 48', comprising a laser-ablated aperture in the column portion 62B having an axis which is orthogonal to the first and second planar surfaces 32' and 34', communicates a distal end of the first microchannel 36' with a first end of the second microchannel 38' to form a single, extended separation compartment.

Further, an aperture 44', laser ablated in the first cover plate portion 62A, enables fluid communication with the first microchannel 36', and a second aperture 46', laser ablated in the second cover plate portion 62C, enables fluid communication with the second microchannel 38'. As described above, when the first and second apertures are used as an inlet and outlet port, respectively, a miniaturized column device is provided having a flow path extending along the combined length of the first and second microchannels.

Detection means can optionally be included in the device of FIG. 5A and FIG. 5B. In one particular embodiment, a first aperture 54' can be laser ablated in the first cover plate portion 62A, and a second aperture 56' can likewise be formed in the second cover plate portion 62C, wherein the apertures are arranged to co-axially communicate with each other and communicate with the conduit means 48' when the flexible substrate 62 is hingeably folded as described above to accurately align the apertures 54' and 56' with the conduit means 48'.

Figure 6:
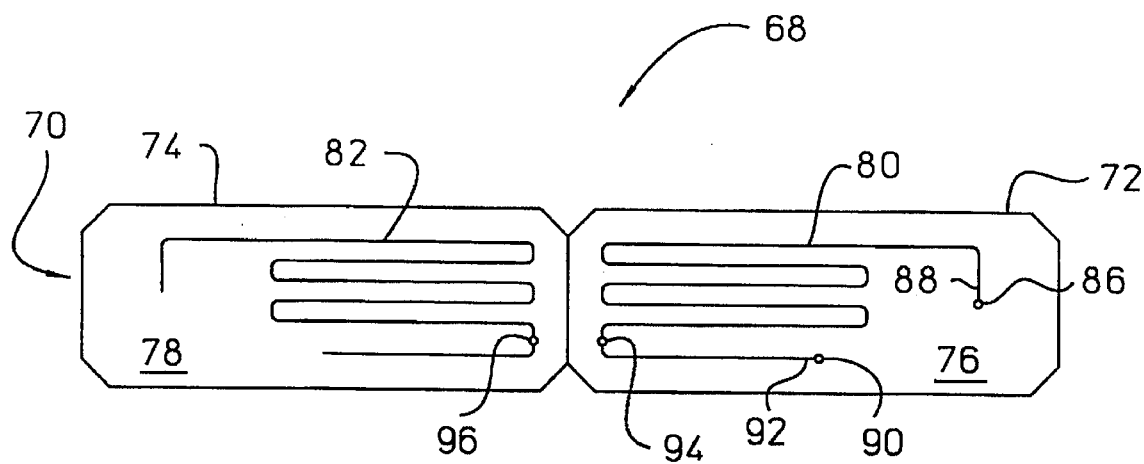
FIG. 6 is plan view of a miniaturized column device constructed according to the invention having first and second component halves.

Referring now to FIG. 6, a miniaturized column for liquid phase analysis of a sample is generally indicated at 68. The miniaturized column 68 is formed by providing a support body 70 having first and second component halves indicated at 72 and 74 respectively. The support body may comprise a substantially planar substrate such as a polyimide film which is both laser ablatable and flexible so as to enable folding after ablation; however, the particular substrate selected is not considered to be limiting in the invention.

The first and second component halves 72 and 74 each have substantially planar interior surfaces, indicated at 76 and 78 respectively, wherein miniaturized column features may be laser ablated. More particularly, a first microchannel pattern 80 is laser ablated in the first planar interior surface 76 and a second microchannel pattern 82 is laser ablated in the second planar interior surface 78. According to the invention, said first and second microchannel patterns are ablated in the support body 70 so as to provide the mirror image of each other.

Figure 7:
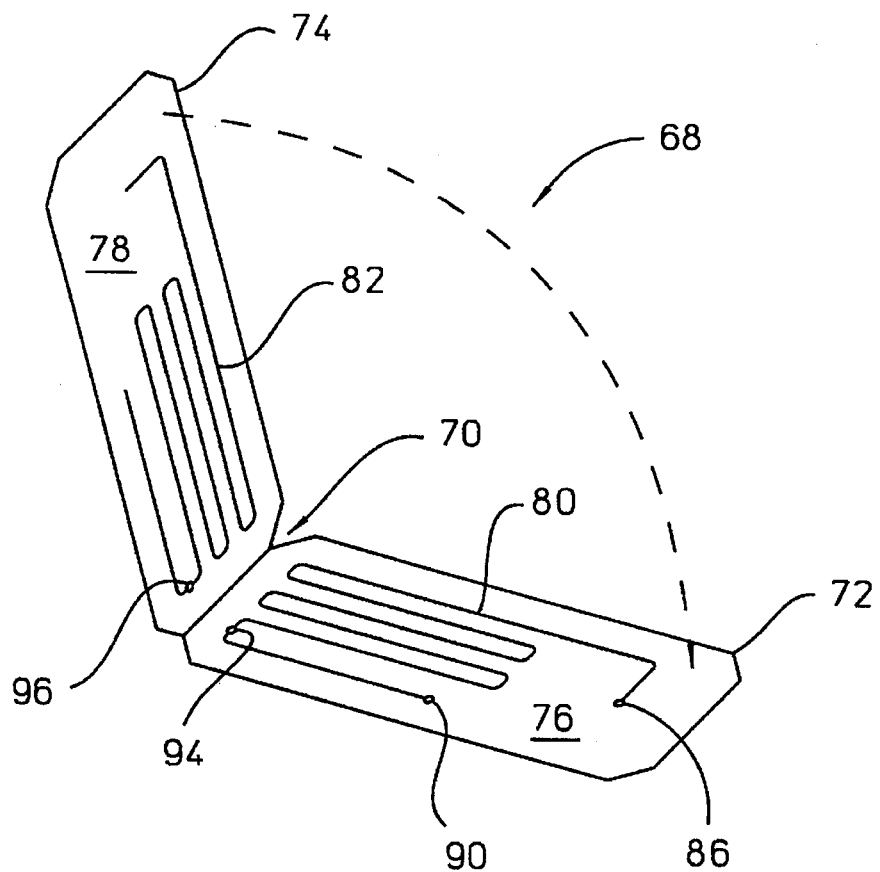
FIG. 7 is a pictorial representation of the column device of FIG. 6 showing the folding alignment of the component halves to form a single device.

Referring now to FIG. 7, a sample processing compartment 84, comprising an elongate bore defined by the first and second microchannel patterns 80 and 82 may be formed by aligning (such as by folding) the first and second component halves 72 and 74 in facing abutment with each other. In the practice of the invention, the first and second component halves may be held in fixable alignment with one another to form a liquid-tight sample processing compartment using pressure sealing techniques, such as by application of tensioned force, or by use of adhesives well known in the art of liquid phase separation devices. It is further contemplated according to the invention to form first and second microchannels 80 and 82 having semi-circular cross-sections whereby alignment of the component halves defines a sample processing compartment 84 having a highly symmetrical circular cross-section to enable enhanced fluid flow therethrough; however, as discussed above, a wide variety of microchannel geometries are also within the spirit of the invention.

In a further preferred embodiment of the invention, it is particularly contemplated to form the support body 70 from a polymer laminate substrate comprising a Kapton® film co-extruded with a thin layer of a thermal plastic form of polyimide referred to as KJ® and available from DuPont (Wilmington, Del.). In this manner, the first and second component halves 72 and 74 may be heat sealed together, resulting in a liquid-tight weld that has the same chemical properties and, accordingly, the same mechanical, electrical and chemical stability, as the bulk Kapton® material.

Referring now to FIG. 6 and FIG. 7, the miniaturized column device 68 further comprises means for communicating associated external fluid containment means (not shown) with the sample processing compartment 84 to provide a liquid-phase separation device. More particularly, a plurality of apertures may be laser ablated in the support body 70, wherein said apertures extend from at least one exterior surface of the support body and communicate with at least one microchannel, said apertures permitting the passage of fluid therethrough. In this regard, an inlet port 86 may be laser ablated in the first component half 72 and communicate with a first end 88 of said first microchannel 80. In the same manner, an outlet port 90 may be ablated in the first component half and communicate with a second end 92 of said first microchannel 80.

As is readily apparent, a liquid phase sample processing device may thereby be formed, having a flow path extending from the first end 88 of the microchannel 80 to the second end 92 thereof, by communicating fluids from an associated source (not shown) through the inlet port 86, passing the fluids through the sample processing compartment 84 formed by the alignment of microchannels 80 and 82, and allowing the fluids to exit the sample processing compartment via the outlet port 92. In this manner, a wide variety of liquid phase analysis procedures may be carried out in the subject miniaturized column device using techniques well known in the art. Furthermore, various means for applying a motive force along the length of the sample processing compartment 84, such as a pressure differential or electric potential, may be readily interfaced to the column device via the inlet and outlet ports, or by interfacing with the sample processing compartment via additional apertures which may be ablated in the support body Inlet port 86 may be formed such that a variety of external fluid and/or sample introduction means may be readily interfaced with the miniaturized column device 68. As discussed in greater detail above, such means include external pressure injection, hydrodynamic injection or electrokinetic injection mechanisms.

Referring now to FIG. 6 and FIG. 7, the miniaturized column device 68 further comprises detection means laser ablated in the support body 70. More particularly, a first aperture 94 is ablated in said first component half 72 and communicates with the first microchannel 80 at a point near the second end thereof. A second aperture 96 is likewise formed in said second component half 74 to communicate with the second microchannel 82. Accordingly, a wide variety of associated detection means may then be interfaced to the sample processing compartment 84 to detect separated analytes of interest passing therethrough, such as by connection of electrodes to the miniaturized column via the first and second apertures 94 and 96.

Accordingly, there have been described several preferred embodiments of a miniaturized column device formed according to the invention by laser ablating microstructures on component parts and aligning the components to form columns having enhanced symmetries. As described in detail above, formation of the subject microchannels in the open configuration enables a wide variety of surface treatments and modifications to be applied to the interior surfaces of the channels before formation of the sample processing compartment. In this manner, a wide variety of liquid phase analysis techniques may be carried out in the composite sample processing compartments thus formed, including chromatographic, electrophoretic and electrochromatographic separations.

Figure 8:
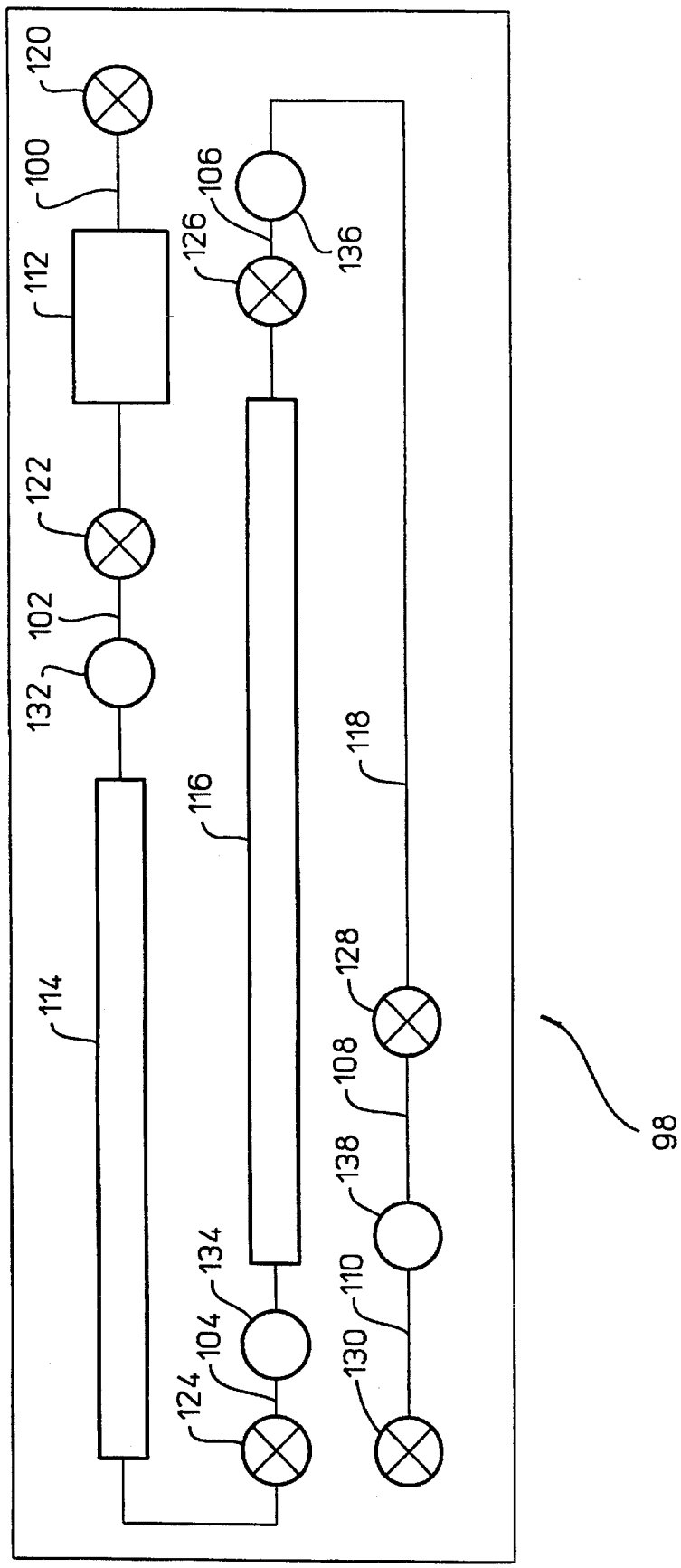
FIG. 8 is a diagram of an exemplary μ-TAS.

FIG. 8 illustrates one embodiment of a μ-TAS. While this embodiment is described for bioanalytical applications, it an object of the invention to provide start-to-finish analysis for any solute species, including small (less than about 1000 molecular weight) and large (greater than about 1000 molecular weight) solute species in complex matrices.

Generally, μ-TAS 98 can be constructed as described in detail above by providing a substrate having first and second planar opposing surfaces and laser ablating a microchannel having more than one sample handling region (100 through 110 and 112 through 118) in the first planar substrate, and optionally having a plurality of laser-ablated access ports (120 through 130) and detection means (132 through 138). A sample processing compartment having sample flow components (100 through 110) and sample treatment components (112 through 118) corresponding to the sample handling regions can be formed by arranging a cover plate over the planar surface (see, e.g., FIG. 1, FIG. 2 and FIG. 3).

Alternatively, μ-TAS 98 may be constructed by providing a support body having first and second component halves with planar interior surfaces, laser ablating mirror images of a microchannel having more than one sample handling region (100 through 110 and 112 through 118) in the interior surfaces of the first and second component interior surfaces, and optionally having laser-ablated access ports (120 through 130) and detection means (132 through 138). A sample processing compartment having sample flow components (100 through 110) and sample treatment components (112 through 118) may be formed by aligning the interior surfaces in facing abutment with each other (see, e.g., FIG. 6 and FIG. 7).

In a further embodiment, μ-TAS 98 may be constructed as described above in reference to FIGS. 5A and 5B by providing a single, flexible substrate having three distinct regions, a column portion, having first and second substantially planar opposing surfaces, a first cover plate portion and a second cover plate portion. Thus, for example, a microchannel having more than one sample handling region (100 through 110 and 112 through 118) can be laser ablated in the first planar surface of the column portion of the flexible substrate. A sample processing compartment is then formed by folding the flexible substrate at the first fold means such that the first cover plate portion covers the first planar surface of the column portion. Alternatively, mirror images of a microchannel having more than one sample handling region (100 through 110 and 112 through 118) can be laser ablated in the first planar surface of the column portion and the interior surface of the first cover portion of the flexible substrate such that a sample processing compartment is formed by folding the flexible substrate at the first fold means as described above by aligning the first planar surface of the column portion with the interior surface of the first cover portion in facing abutment with each other.

Generally, the sample handling region of the microchannel from which the sample flow components (100 through 110) are formed is elongate and semi-circular in geometry. However, as described in greater detail above, the microchannel may be formed in a wide variety of channel geometries including semi-circular, rectangular, rhomboid, and the like, and the channels may be formed in a wide range of aspect ratios. The sample handling region of the microchannel from which the sample treatment components (112 through 118) are formed is typically rectangular; however, it may be laser ablated in any desired geometry. Furthermore, in any particular μ-TAS, the sample handling regions of the microchannel may be formed in any combination of geometries including rectangular, square, triangular, and the like. In addition, while the μ-TAS illustrated in FIG. 8 contains sample flow components with high aspect ratios (i.e., aspect ratios in which the depth of the microstructure is greater than the width) and sample treatment components with low aspect ratios (i.e., aspect ratios in which the width of the microstructure is greater than the depth), this is not intended to be limiting. For example, sample treatment components may have high aspect ratios, as in fourth sample treatment component 118.

As depicted in FIG. 8, μ-TAS 98 is a serial arrangement of alternating sample flow components 100 through 110 and sample treatment components 112 through 118. Optionally, detection means 130 through 138 are disposed along the sample flow components. The detection means may be formed in the cover plate, the substrate itself, or both the cover plate and the substrate, as described in greater detail above.

In addition, optional access ports (120 through 130) depicted in FIG. 8 are disposed along the sample flow components. The access ports allow the fluid communication of the sample flow component with, for example, external liquid reservoirs or mechanical valving necessary for the introduction or removal of samples, buffers and the like from the sample flow component as required to effect sample preparation by the μ-TAS. External hardware may also be interfaced to the subject μ-TAS to provide liquid handling capabilities, and a variety of means for applying a motive force along the length of the sample processing compartment may be associated with the μ-TAS. Thus, access ports may be in divertable and switchable fluid communication with a valving manifold such that a valve in communication with an access port can be individually "actuated," i.e., opened to allow flow or closed to prevent flow through the access port.

In particular reference to FIG. 8, μ-TAS 98 depicted therein contains first access port 120 by which sample may be introduced into first sample flow component 100 that is in fluid communication with first sample treatment component 112. The sample may be directly added to the sample flow component via first access port 120 without prior processing. Optionally, fist access port 120 may be interfaced with an external pre-column sample preparation device, e.g., a filtration device.

In one embodiment, sample treatment component 112 performs a filtration function and may be filled with a porous medium made of particles, sheets or membranes. In a preferred embodiment, the medium has an effective pore size of between 45 µm and 60 µm. Preferably, the medium is biocompatible and may be made from such materials as nylon, cellulose, polymethylmethacrylate, polyacrylamide, agarose, or the like. In an alternative embodiment, the filtration function may be performed by an in-line device prior to introduction of the sample into sample flow component 112.

In the particular embodiment depicted in FIG. 8, sample treatment component 112 is designed to serve a "capture" function. Thus, sample treatment component 112 can be an affinity chromatography, ion exchange chromatography, a complexation reaction or any such quantal chromatographic technique (i.e., a chromatographic technique that could otherwise be performed in a batch mode rather than with a flowing sample stream). An affinity chromatography matrix may include a biological affiant, an antibody, a lectin, enzyme substrate or analog, enzyme inhibitor or analog, enzyme cofactor or analog, a capture oligonucleotide, or the like, depending on the nature of the sample. The ion exchange matrix may be an anionic or cationic ion exchange medium. Complexation reactions may include boronate reactions, dithiol reactions, metal-ion reactions, for example, with porphyrin or phenanthroline, or other reactions in which the sample is reversibly reacted with the chromatography matrix.

First and second access ports 120 and 122 are respectively disposed upstream and downstream from first sample treatment component 112. When first access port 120 is used as an input port and second access port is used as a withdrawal port, sample treatment component 112 can be isolated from downstream µ-TAS sample handling regions. Thus, while a sample is loaded onto sample treatment component 112, extraneous materials which are flushed from the sample treatment component during analyte capture may be withdrawn and, in this manner, prevented from entering downstream µ-TAS sample handling regions. Alternatively, second access port 122 may be used as an fluid input port to provide flow regulation, sample derivatization, or other like function when connected to a source of fluid which may be an external fluid source or an on-device fluid reservoir compartment Once a sample has been introduced into first sample flow component 112, sample flow may be effected by way of an external motive means which is interfaced with first access port 120. Alternatively, sample flow into sample treatment component 112 may be effected by activation of an on-device motive means, e.g., an on-device fluid reservoir compartment.

First detection means 132 may be in direct or indirect communication with second sample flow component 102 downstream from first sample treatment component 112. First detection means 132 can be used to monitor the presence of a sample in sample flow component 102 which is to be loaded onto second sample treatment component 114 or to monitor sample elution from first sample treatment component 112. In the latter case, it is preferred that first detection means 132 is placed in second sample flow component 102 upstream from second access port 122.

In the particular embodiment depicted in FIG. 8, second sample treatment component 114 serves to desalt or neutralize the analyte eluted from first sample treatment component 112. Thus, second sample treatment component 114 may be an electrophoretic desalting, pH neutralizing, size exclusion chromatography component, or the like.

As with first sample treatment component 112, second sample treatment component 114 is flanked by second and third access ports 122 and 124. First, second and third access ports 120, 122 and 124 may be used in any combination of inlet and outlet ports. Generally, once the sample has been eluted from first sample treatment component 112 and loaded onto second sample treatment component 114, second access port 122 serves as an inlet port and third access port 124 serves as an outlet port, thereby isolating second sample treatment component 114 from downstream µ-TAS sample handling regions. In order to prevent backflow into first sample treatment component 112, first access port 120 can be closed.

As exemplified in FIG. 8, third sample treatment component 116 has been configured as an analyte focussing and pre-final sample processing compartment. As such, third sample treatment component 116 can be an isoelectric focusing component, an isotachophoretic sample stacking component, or the like. Again, third sample treatment component 116 is flanked by third and fourth access ports 124 and 126, which may be operated in a manner similar to that described for access port pairs 120/122 and 122/124 to isolate third sample treatment component 116 from downstream sample handling regions. Second and third detection means 134 and 136 may also be used as described above for first detection means 132.

Fourth sample treatment component 118 may include single or multiple functions selected from chromatographic, electrophoretic, or electro-chromatographic functions. Although only one sample treatment component 118 is shown in FIG. 8, multiple components of various dimensions can be laser ablated in continuum and specifically prepared as different sample processing functions in series. Examples of chromatographic functions which may be included in fourth sample treatment component 118 are reverse phase chromatography, hydrophobic interaction chromatography, affinity chromatography, size exclusion chromatography, ion exchange chromatography, chiral separation chromatography, and the like. For chromatographic functions, the stationary phase may be bonded or otherwise adhered to the surface of a particle or to the walls of the component. Examples of electrophoretic chromatography include open tubular electrophoresis, micellar electrokinetic capillary electrophoresis (see, Terabe et al. (1985) Anal. Chem. 57:834–841), capillary chiral electrophoresis, and the like. Open tubular electrophoresis includes bonded phase, dynamic deactivation using any of a variety of inorganic or organic reagents, isoelectric focussing, and the like. Micellar electrokinetic capillary chromatography may be done using surfactants such as sodium dodecyl sulfate, cetyl ammonium bromide, alkyl glucosides, alkyl maltosides, zwitterionic surfactants such as 3-[(3-cholamidopropyl)-dimethylammonio]-1-propane sulfonate ("CHAPS"), 3-[(3-cholamidopropyl)-dimethylammonio]-2-hydroxy-1-propane sulfonate ("CHAPSO"), or the like. Capillary chiral electrophoresis may be done using reagents such as cyclodextrins, crown ethers, bile salts, or the like.

Fourth detection means 138 can be situated in the sample flow component that is downstream from fourth sample treatment component 118. The detection means may be ablated into the substrate, cover plate, or both the substrate and the cover plate.

In a further optional embodiment of the µ-TAS, fifth access port 128 may serve one or more of a number of functions. As described above, fifth access port 128 may serve as an outlet port for fourth sample treatment component 118. It may optionally be attached to an external or on-device fluid reservoir compartment, thereby providing a means to regulate sample flow rates through the µ-TAS or a means to introduce reagents into fifth sample flow component 108 which react with the sample to facilitate sample detection by fourth detection means 138.

Sixth access port 130 may serve one or more of a variety of functions as well including withdrawal of sample after final detection. Optionally, as with fifth access port 128, sixth access port 130 may be attached to a fluid reservoir compartment. In addition, sixth access port 130 may interface additional laser ablated microstructures for communicating a sample droplet to a post-column collection device.

Accordingly, a novel miniaturized column device and a µ-TAS have been described which are laser ablated into a substrate other than silicon or silicon dioxide materials, and which avoid several major problems which have come to be associated with prior attempts at providing micro-column devices. The use of laser ablation techniques in the practice of the invention enables highly symmetrical and accurately defined micro-column device and µ-TAS to be fabricated in a wide class of polymeric and ceramic substrates to provide a variety of miniaturized liquid-phase analysis systems. In this regard, a miniaturized column and a µ-TAS may be provided which have micro-capillary dimensions (ranging from 5–200 µm in diameter) and column detection path lengths of up to 1 mm or greater. This feature has not been attainable in prior attempts at miniaturization, such as in capillary electrophoresis, without substantial engineering of a device after capillary formation. Further, laser ablation of a miniaturized column or a µTAS in inert substrates such as polyimides avoids the problems encountered in prior devices formed in silicon or silicon dioxide-based materials. Such problems include the inherent chemical activity and pH instability of silicon and silicon dioxide-based substrates which limits the types of separations capable of being performed in those devices.

A miniaturized column device or a µ-TAS may be formed by laser ablating a set of desired features in a selected substrate using a step-and-repeat process to form discrete units. It is particularly contemplated to laser ablate the subject devices in condensation polymer substrates including polyimides, polyamides, poly-esters and poly-carbonates. Further, the instant invention may be practiced using either a laser ablation process or a LIGA process to form templates encompassing a set of desired features, whereby multiple copies of a miniaturized column or a µ-TAS may be mass-produced using injection molding techniques well known in the art. More particularly, it is contemplated herein to form a miniaturized column or a µ-TAS by injection molding in substrates comprised of materials such as the following: polycarbonates; polyesters, including poly(ethylene terephthalate) and poly(butylene terephthalate); polyamides, (such as nylons); polyethers, including polyformaldehyde and poly(phenylene sulfide); polyimides, such as Kapton® and Upilex®; polyolefin compounds, including ABS polymers, Kel-F copolymers, poly(methyl methacrylate), poly(styrene-butadiene) copolymers, poly(tetrafluoroethylene), poly(ethylene-vinyl acetate) copolymers, poly(N-vinylcarbazole) and polystyrene.

Laser ablation of microchannels in the surfaces of the above-described substrates has the added feature of enabling a wide variety of surface treatments to be applied to the microchannels before formation of the sample processing compartment. That is, the open configuration of laser-ablated microchannels produced using the method of the invention enables a number of surface treatments or modifications to be performed which are not possible in closed format constructions, such as in prior micro-capillaries. More specifically, laser ablation in condensation polymer substrates provides microchannels with surfaces featuring functional groups, such as carboxyl groups, hydroxyl groups and amine groups, thereby enabling chemical bonding of selected species to the surface of the subject microchannels using techniques well known in the art. Other surface treatments enabled by the open configuration of the instant devices include surface adsorptions, polymer graftings and thin film deposition of materials such as diamond or sapphire to microchannel surfaces using masking and deposition techniques and dynamic deactivation techniques well known in the art of liquid separations.

The ability to exert rigid computerized control over the precise the present laser ablation processes enables extremely precise microstructure formation, which, in turn, enables the formation of a miniaturized column or a µ-TAS having features ablated in two substantially planar components wherein those components may be aligned to define a composite sample processing compartment of enhanced symmetry and axial alignment. In this regard, it is contemplated to provide a further embodiment of the invention wherein laser ablation is used to create two component halves which, when folded or aligned with one another, define a single miniaturized column device or µ-TAS.

The above-described miniaturized column devices and/or µ-TAS may be provided in thermal communication with any temperature control device known in the art. Preferably, the temperature control device is a thermoelectric temperature control device; more preferably the temperature control device is a thermoelectric temperature control device having Peltier elements.

Figure 9A:
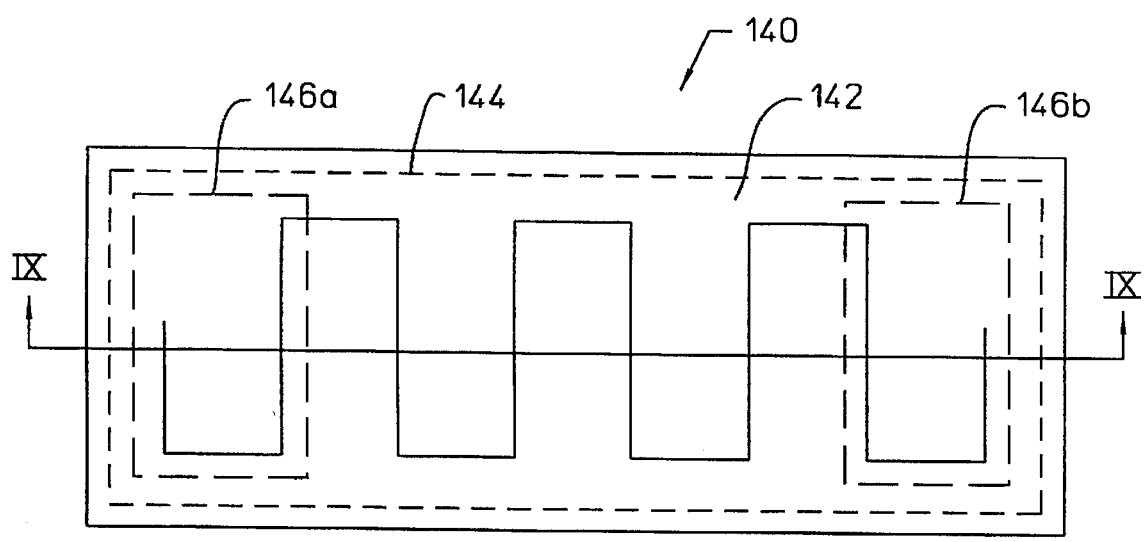
FIG. 9A is a top plan view of a miniaturized column device or μ-TAS in thermal contact with a pair of temperature control devices.
Figure 9B:
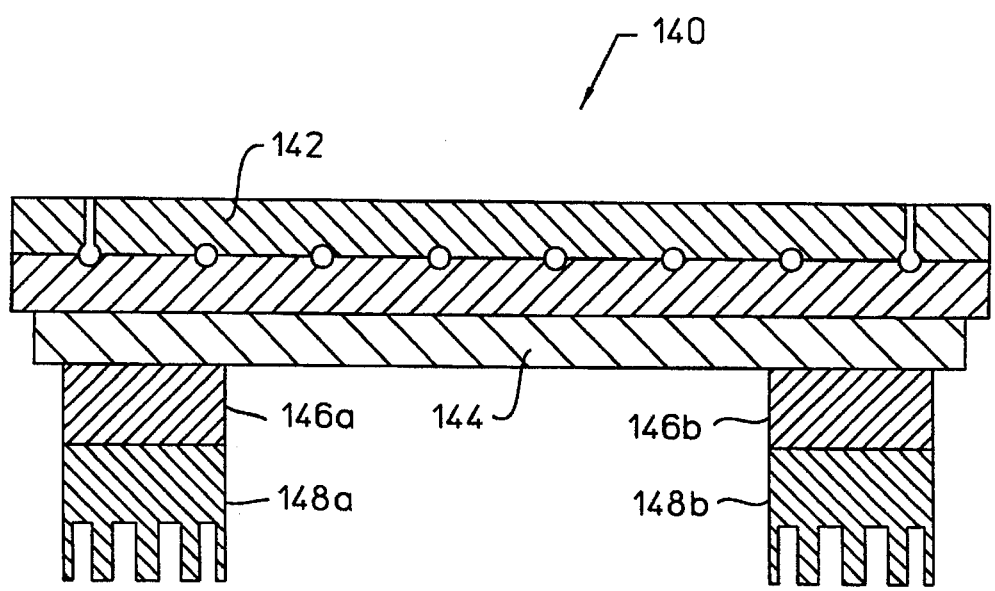
FIG. 9B is a cross-sectional side view of a miniaturized column device or μ-TAS in thermal contact with a pair of temperature control devices as shown in FIG. 9A, taken along lines IX—IX.

Referring to FIG. 9A and FIG. 9B, a substrate into which a miniaturized column device or µ-TAS has been laser ablated and which is in thermal contact with a pair of temperature control devices is generally indicated at 140. The substrate 142 is optionally in direct thermal contact with thermally conductive plate 144 interposed between the substrate and the temperature control devices 146a and 146b. Plate 144 may be any thermally conductive material, such as alumina, copper or the like. As depicted in FIG. 9A and FIG. 9B, temperature control devices 146a and 146b are solid state heat pumps, also referred to as Peltier devices. As is well known to those skilled in the art, Peltier devices are solid state devices that operate as heat pumps and thus may be used to absorb heat from the substrate, thereby cooling the substrate or, in the alternative, may be used to generate heat and thereby warm the substrate. Peltier devices may be used in a single-stage configuration as depicted in FIG. 9B or in a multi-stage ("stacked") configuration to increase the heat exchange capacity of the system. Such devices may be obtained from, e.g., ITI Ferrotec (Chelmsford, Mass.), Cambion (Tampa, Fla.) or Melcor Corp. (Trenton, N.J.).

Temperature control devices 146a and 146b may also be placed in thermal contact with heat exchange modules 148a and 148b, in order to assist the transfer of heat to or from substrate 142 to temperature control devices 146a and 146b. Thermal contact of the components may be augmented by the use of a thermally conductive paste from, e.g., Omega Engineering, Stamford, Conn.

Temperature control devices may be used to regulate the temperature of the substrate in thermal contact therewith.

The temperature control devices may be used to regulate the temperature by heating or cooling a localized, regional or coterminous portion of the substrate. In addition, the temperature control device may be used to create temporal temperature gradients, i.e., localized or regional changes in temperature over time. Alternatively, as depicted in FIG. 9A and 9B, two temperature control devices 146a and 146b may be placed in thermal contact with thermally conductive plate 144 configured to generate a spacial temperature gradient in substrate 142 that is in thermal contact with the thermally conductive plate. Thus, if the temperature of temperature control device 146a is set at $T_1$ and the temperature of temperature control device 146b is set at $T_2$, the gradient across thermally conductive plate 144 and substrate 142 will range between $T_1$ and $T_2$.

Figure 10A:
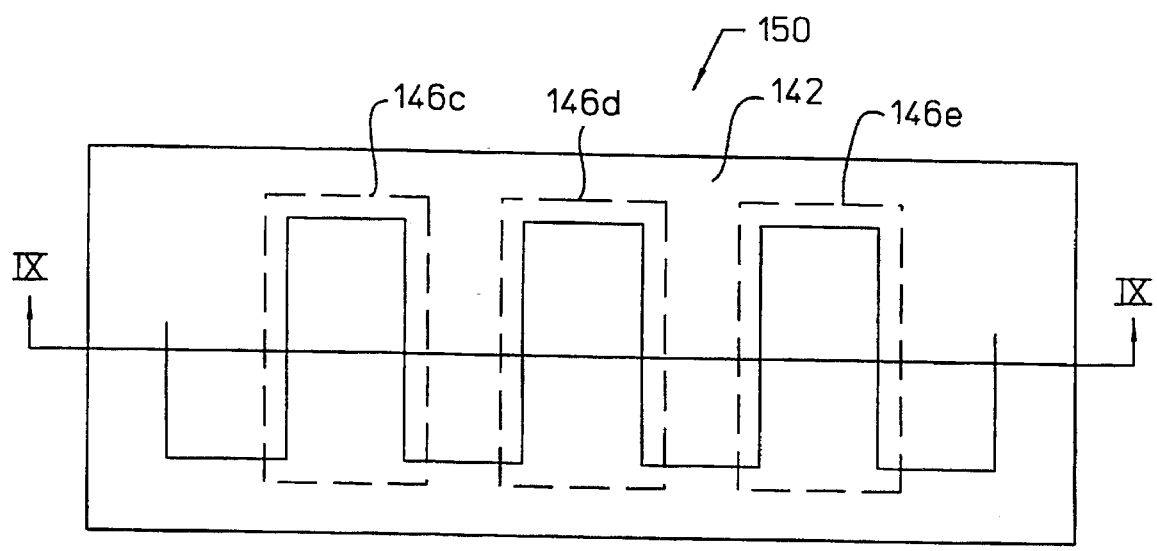
FIG. 10A is a top plan view of a miniaturized column device or a μ-TAS in thermal contact with a plurality of temperature control devices.
Figure 10B:
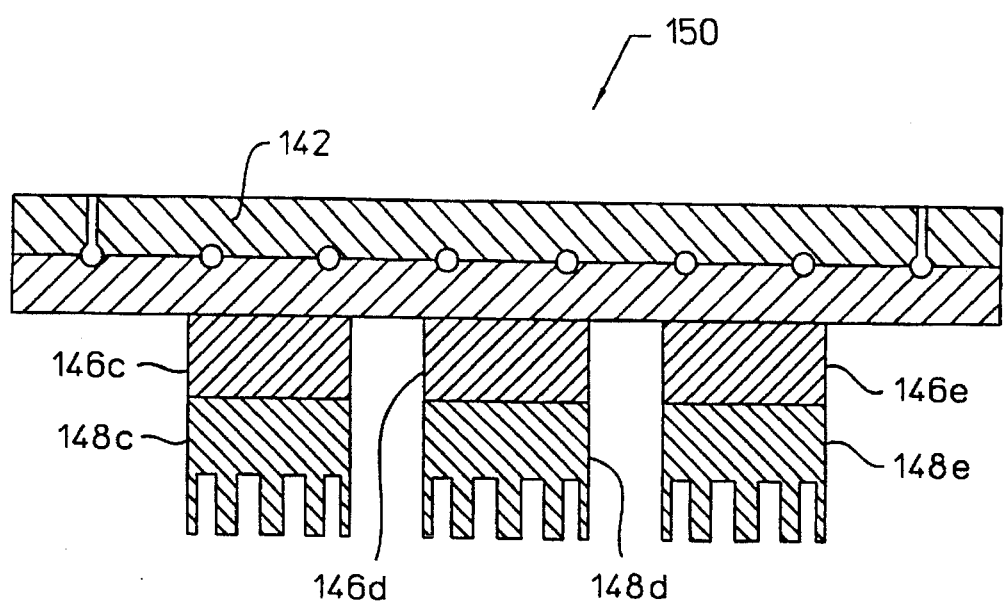
FIG. 10B is a cross-sectional side view of a miniaturized column device or a μ-TAS in thermal contact with a plurality of temperature control devices as depicted in FIG. 10A, taken along lines X—X.

In FIG. 10A and FIG. 10B a substrate into which a miniaturized column device or μ-TAS has been laser ablated and which in thermal contact with a plurality of temperature control devices is generally indicated at 150. In this configuration, temperature control devices 146c, 146d and 146e are placed in thermal contact with substrate 142 so that a localized temperature control effect may be achieved. Temperature control devices 146c, 146d and 146e may also be placed in thermal contact with heat exchange modules 148c, 148d and 148e, in order to assist the transfer of heat to or from substrate 142 to temperature control devices 146. Thus, depending the effect to be achieved, each of temperature control devices 146c, 146d and 146e may independently be set to the same or different temperatures. A temperature step-gradient may be achieved, for example, if temperature $T_{146c} > T_{146d} > T_{146e}$. Alternatively, in a μ-TAS device, a temperature control device may be placed in thermal communication with a region of the device that corresponds to a sample treatment compartment, a sample flow department or both. Sample processing efficiency may be enhanced by independently regulating the temperature of each sample treatment compartment and each sample flow compartment, either by heating or cooling.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

We claim:

1. A liquid phase sample separation apparatus comprising:
   (a) a miniaturized column device comprising
      (i) a substrate having first and second substantially planar opposing surfaces wherein said substrate is comprised of a material other than silicon or silicon dioxide, said substrate having a microchannel laser-ablated in the first planar surface,
      (ii) a cover plate arranged over the first planar surface, said cover plate in combination with the microchannel defining an elongate separation compartment, and
      (iii) at least one inlet port and at least one outlet port communicating with the separation compartment, said ports enabling the passage of fluid from an external source through the separation compartment; and
   (b) a temperature control device in thermal communication with the miniaturized column device.

2. The apparatus of claim 1, wherein the temperature control device comprises a thermoelectric temperature control device.

3. The apparatus of claim 2, wherein the thermoelectric temperature control device comprises Peltier elements.

4. The apparatus of claim 1, wherein the temperature control device is coterminous with the miniaturized column device.

5. The apparatus of claim 1, comprising a plurality of temperature control devices in thermal communication with the miniaturized column device, thereby enabling localized temperature control.

6. The apparatus of claim 5, wherein the temperature control devices are in thermal communication with the miniaturized column device, thereby enabling the formation of a temperature gradient along the length of the miniaturized column device.

7. A liquid phase sample separation apparatus comprising:
   (a) a miniaturized column device comprising
      (i) a substrate having first and second substantially planar and parallel opposing surfaces, wherein said substrate is comprised of a material other than silicon or silicon dioxide, said substrate having first and second microchannels respectively laser ablated in the first and second planar surfaces,
      (ii) first and second cover plates disposed respectively over the first and second planar surfaces, said cover plates in combination with the first and second microchannels defining first and second elongate separation compartments, and
      (iii) a conduit means for communicating the first and second separation compartments with each other, thereby forming a single continuous separation compartment, said conduit means comprising an aperture in the substrate having an axis which is orthogonal to the planar surfaces; and
   (b) a temperature control device in thermal communication with the column device.

8. The apparatus of claim 7, wherein the temperature control device comprises a thermoelectric temperature control device.

9. The apparatus of claim 8, wherein the thermoelectric temperature control device comprises Peltier elements.

10. The apparatus of claim 7, wherein the temperature control device is coterminous with the miniaturized column device.

11. The apparatus of claim 7, comprising a plurality of temperature control devices in thermal communication with the miniaturized column device, thereby enabling localized temperature control.

12. The apparatus of claim 11, wherein the temperature control devices are in thermal communication with the miniaturized column device, thereby enabling the formation of a temperature gradient along the length of the miniaturized column device.

13. A liquid phase sample separation apparatus comprising:
   (a) a miniaturized column device comprising
      (i) a support body formed from a substrate comprised of a material other than silicon or silicon dioxide, said support body having first and second component halves each having substantially planar interior surfaces,
      (ii) a first microchannel laser-ablated in the interior surface of the first support body half and a second microchannel laser-ablated in the interior surface of the second support body half, wherein each said microchannel is so arranged as to provide the mirror image of the other, (iii) a separation compartment comprising an elongate bore formed by aligning the interior surfaces of the support body halves in facing abutment with each other whereby the microchannels define said elongate bore, and (iv) at least one inlet port and at least one outlet port communicating with the separation compartment, said ports enabling the passage of fluid from an external source through the separation compartment; and (b) a temperature control device in thermal communication with the column device.

14. The apparatus of claim 13, wherein the temperature control device comprises a thermoelectric temperature control device.

15. The apparatus of claim 14, wherein the thermoelectric temperature control device comprises Peltier elements.

16. The apparatus of claim 13, wherein the temperature control device is coterminous with the miniaturized column device.

17. The apparatus of claim 13, comprising a plurality of temperature control devices in thermal communication with the miniaturized column device, thereby enabling localized temperature control.

18. The apparatus of claim 17, wherein the temperature control devices are in thermal communication with the miniaturized column device, thereby enabling the formation of a temperature gradient along the length of the miniaturized column device.

19. A liquid phase sample separation apparatus comprising:

(a) a miniaturized total analysis system (μ-TAS) comprising a miniaturized column device comprising (i) a substrate having first and second substantially planar opposing surfaces wherein said substrate is comprised of a material other than silicon or silicon dioxide, said substrate having a first microchannel laser-ablated in the first planar surface, wherein said first microchannel comprises more than one sample handling region, (ii) a cover plate arranged over the first planar surface, said cover plate in combination with the first microchannel forming a first sample processing compartment, wherein the sample handling regions define a sample flow component in fluid communication with a sample treatment component, and (iii) at least one inlet port and at least one outlet port communicating with the first sample processing compartment, said inlet and outlet ports enabling the passage of fluid from an external source through the sample processing compartment; and (b) a temperature control device in thermal communication with the miniaturized column device.

20. The apparatus of claim 19, wherein the temperature control device comprises a thermoelectric temperature control device.

21. The apparatus of claim 20, wherein the thermoelectric temperature control device comprises Peltier elements.

22. The apparatus of claim 19, wherein the temperature control device is coterminous with the miniaturized column device.

23. The apparatus of claim 19, comprising a plurality of temperature control devices in thermal communication with the miniaturized column device, thereby enabling localized temperature control.

24. The apparatus of claim 23, wherein the temperature control devices are in thermal communication with the miniaturized column device, thereby enabling the formation of a temperature gradient along the length of the miniaturized column device.

* * * * *